(12) United States Patent
Dayal et al.

(10) Patent No.: US 10,496,877 B2
(45) Date of Patent: Dec. 3, 2019

(54) DEVICE AND METHOD OF CHARACTERIZING MOTION

(71) Applicants: STMicroelectronics, Inc., Coppell, TX (US); STMicroelectronics S.r.l., Agrate Brianza (IT)

(72) Inventors: Sankalp Dayal, Santa Clara, CA (US); Davide Giacalone, San Gregorio di Catania (IT)

(73) Assignees: STMICROELECTRONICS, INC., Coppell, TX (US); STMICROELECTRONICS S.R.L., Agrate Brianza (IT)

( * ) Notice: Subject to any disclaimer, the term of this patent is extended or adjusted under 35 U.S.C. 154(b) by 106 days.

(21) Appl. No.: 15/458,755

(22) Filed: Mar. 14, 2017

(65) Prior Publication Data

US 2018/0267073 A1  Sep. 20, 2018

(51) Int. Cl.
*A61B 5/11* (2006.01)
*G06K 9/00* (2006.01)
*A61B 5/00* (2006.01)

(52) U.S. Cl.
CPC ........ *G06K 9/00342* (2013.01); *A61B 5/1123* (2013.01); *A61B 5/7264* (2013.01); *G06K 9/00543* (2013.01); *A61B 5/002* (2013.01); *A61B 5/681* (2013.01); *A61B 5/6831* (2013.01); *A61B 5/6898* (2013.01); *A61B 5/7225* (2013.01); *A61B 5/7246* (2013.01); *A61B 5/7267* (2013.01); *A61B 2562/0204* (2013.01); *A61B 2562/028* (2013.01); *A61B 2562/029* (2013.01); *A61B 2562/0219* (2013.01); *A61B 2562/0247* (2013.01)

(58) Field of Classification Search
CPC ............ G01P 13/00; G01P 1/12; G01P 15/00
See application file for complete search history.

(56) References Cited

U.S. PATENT DOCUMENTS

| | | | | |
|---|---|---|---|---|
| 2009/0234614 A1* | 9/2009 | Kahn | .................. | G02C 5/001 702/141 |
| 2011/0316888 A1* | 12/2011 | Sachs | .................. | G06F 1/1626 345/667 |
| 2014/0288681 A1* | 9/2014 | Watanabe | ............ | A61B 5/6828 700/91 |
| 2015/0018014 A1* | 1/2015 | Phan | .................... | H04W 4/027 455/456.3 |
| 2015/0140524 A1* | 5/2015 | Giraud-Carrier | ...... | A47G 23/10 434/127 |

(Continued)

*Primary Examiner* — Manuel L Barbee
(74) *Attorney, Agent, or Firm* — Slater Matsil, LLP

(57) ABSTRACT

In an embodiment, a device may include a first sensor configured to generate first sensor data during a first time period and a second time period; a second sensor configured to be disabled during the first time period, the second sensor further being configured to generate second sensor data during the second time period; and a processor configured to determine a characteristic of the first sensor data during the first time period. The device may further include a classifying circuit configured to determine, during the first time period, whether the device has changed state based on the characteristic of the first sensor data, the classifying circuit further being configured to cause the second sensor to be enabled in response to a change in a state of the device.

20 Claims, 7 Drawing Sheets

(56) References Cited

U.S. PATENT DOCUMENTS

2016/0051167 A1\* 2/2016 Saha ................... A61B 5/1123
                                                    702/141
2016/0189534 A1\* 6/2016 Wang ..................... G08C 17/00
                                                    340/870.16

\* cited by examiner

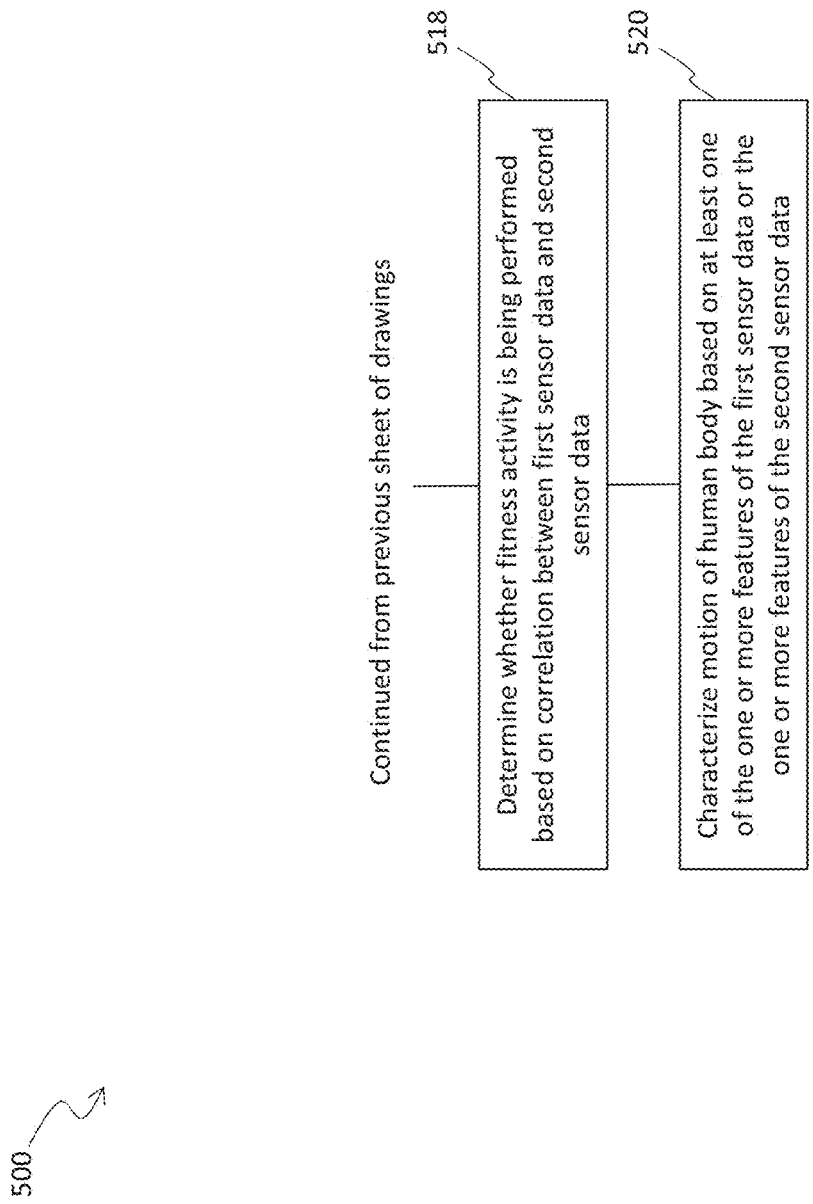

DEVICE AND METHOD OF CHARACTERIZING MOTION

TECHNICAL FIELD

The present disclosure relates generally to sensors, and, in particular embodiments, to a device and method of characterizing motion.

BACKGROUND

Wearable electronic devices have gained popularity among consumers. A wearable electronic device may track user's activities using a variety of sensors and help the user to maintain a healthy life style. In order to determine a user's activities, a wearable electronic device collects activity data and runs computations on that data. It may be desirable to provide a wearable electronic device that is configured to accurately monitor, detect, and characterize (or classify) the motion of the human body based on the motion of the device in real-time and with low power consumption.

SUMMARY

In an embodiment, a device may include a first sensor configured to generate first sensor data during a first time period and a second time period; a second sensor configured to be disabled during the first time period, the second sensor further being configured to generate second sensor data during the second time period; and a processor configured to determine a characteristic of the first sensor data during the first time period. The device may further include a classifying circuit configured to determine, during the first time period, whether the device has changed state based on the characteristic of the first sensor data, the classifying circuit further being configured to cause the second sensor to be enabled in response to a change in a state of the device.

In an embodiment, a method may include generating first sensor data during a first time period; determining whether an electronic device has changed state based on the first sensor data, wherein a transition from the first time period to a second time period occurs in response to a determination that the electronic device has changed state; and generating the first sensor data and second sensor data during the second time period. The method may further include determining one or more features of each of the first sensor data and the second sensor data; and characterizing a motion of a human body based on at least one of the one or more features of the first sensor data or the one or more features of the second sensor data.

In an embodiment, a device may include an accelerometer configured to generate accelerometer data during a first state of the device and a second state of the device; a sensor, different from the accelerometer, configured to generate sensor data during the second state of the device; and a processor configured to determine one or more features of the accelerometer data and one or more features of the sensor data during the second state of the device. The device may further include a classifying circuit configured to characterize a motion of a human body based on at least one of the one or more features of the accelerometer data and the one or more features of the sensor data.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF ILLUSTRATIVE EMBODIMENTS

The making and using of various embodiments are discussed in detail below. It should be appreciated, however, that the various embodiments described herein are applicable in a wide variety of specific contexts. The specific embodiments discussed are merely illustrative of specific ways to make and use various embodiments, and should not be construed in a limited scope.

Recent advances in microelectromechanical systems (MEMS) technology has resulted in the combination of high precision and integration of a plurality of such sensors with control electronics in a small footprint and with low power consumption (e.g. relative to early development of MEMS technology). The rapid growth of MEMS technology has generated a host of diverse developments in many different fields, ranging from automotive, power and fuels, manufacturing, aerospace to healthcare, pharmaceuticals, consumer products, and bio-engineering, to name a few. Additionally, MEMS technology has been applied to the field of human fitness. In such a scenario, it may be useful for an individual engaged in a fitness activity to monitor, save, share, and adapt a fitness activity in an attempt to improve the effectiveness of the fitness activity.

Figure 1:
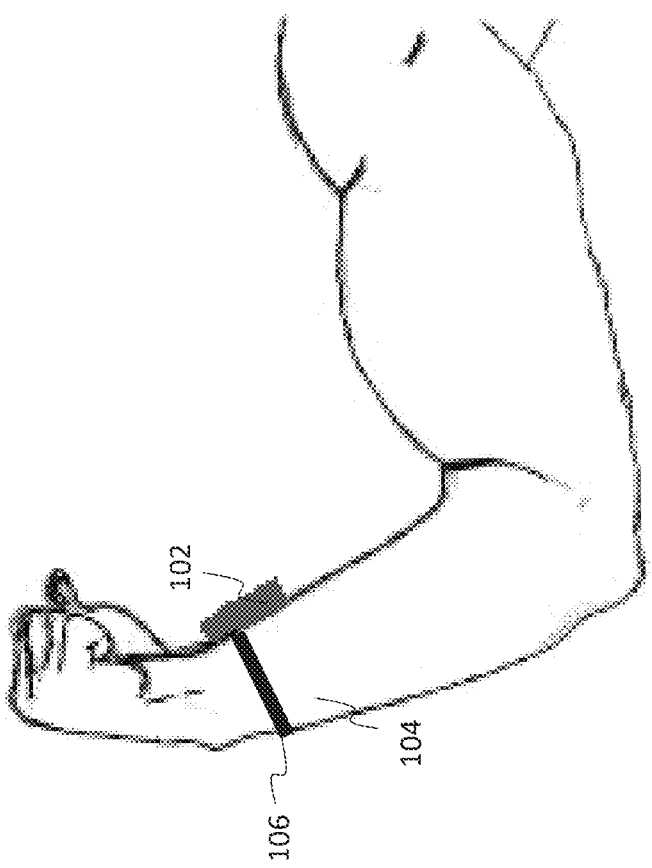
FIG. 1 shows an electronic device secured to a part of a human body, in accordance with an embodiment.

FIG. 1 shows an electronic device 102 secured to a part of a human body 104, in accordance with an embodiment. In the example shown in FIG. 1, the electronic device 102 is secured by a band 106 to a wrist or forearm of a human body; however, in other embodiments, the electronic device 102 may be secured to another part of the human body, such as the biceps, triceps, chest, or waist, as examples.

The electronic device 102 may be a wearable electronic device, examples being a smart watch, fitness band, mobile phone (e.g. running a fitness application), among others. In some embodiments, the electronic device 102 may be an Internet of Things (IoT) device configured to be communicatively coupled with at least one other device through a wireless communications channel (e.g. Wi-Fi, Bluetooth, or the like).

The electronic device 102 may include a plurality of sensors (e.g. MEMS transducers) formed therein. As an example, one or more accelerometers, gyroscopes, pressure sensors, force sensors, humidity sensors, or microphones may be included in the electronic device 102. There may be a need for the electronic device 102 to accurately monitor, detect, and characterize (or classify) the motion of the human body based on the motion of the electronic device 102 in real-time and with low power consumption (e.g. relative to currently available methods). Such real-time, low power, and accurate monitoring, detection, and characterization of the motion of the human body may be accomplished by using the plurality of sensors included in the electronic device 102.

Figure 2:
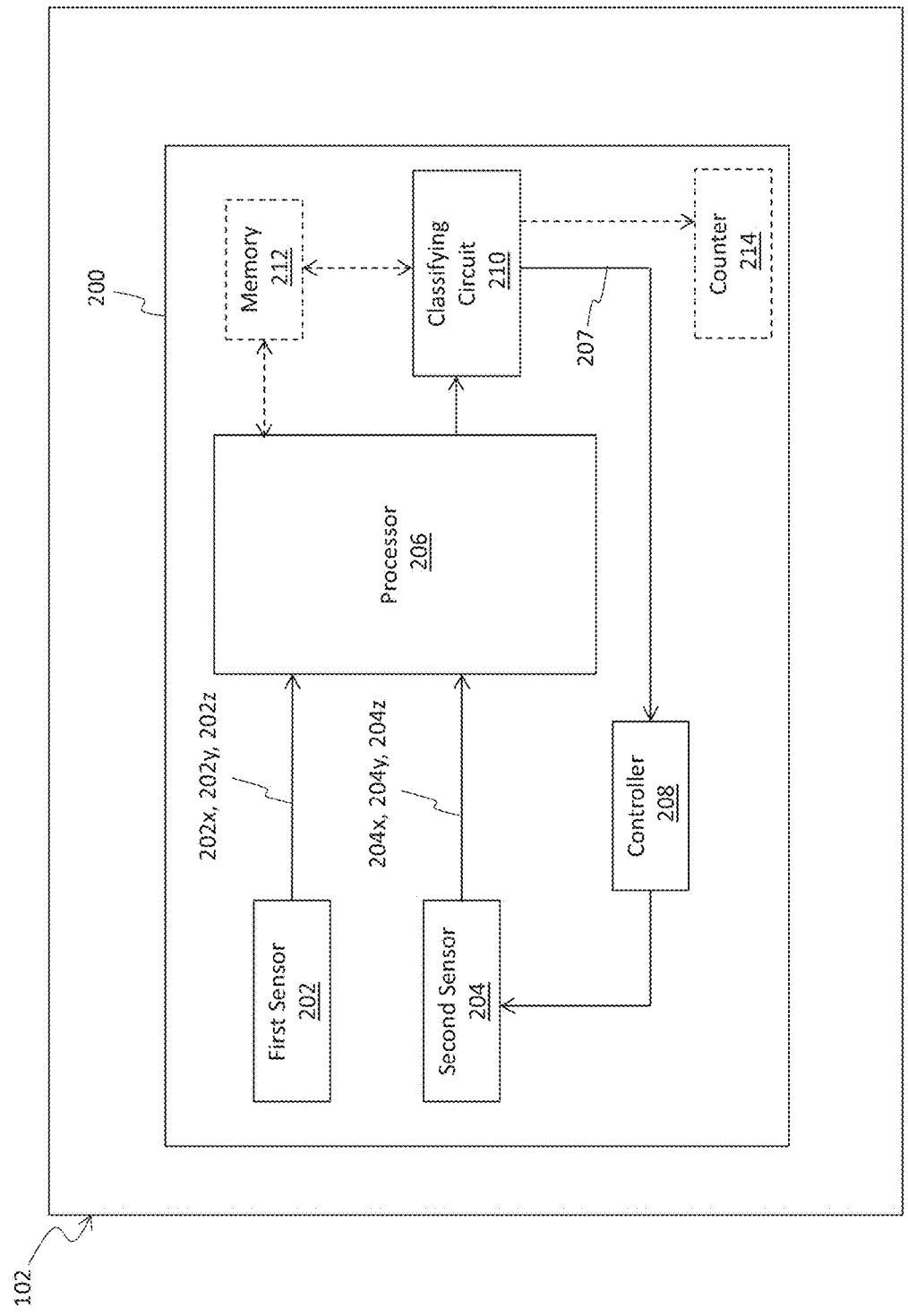
FIG. 2 shows a block diagram of the electronic device shown in FIG. 1, including a first sensor, a second sensor, a processor, a controller, and a classifying circuit, in accordance with an embodiment.
Figure 5:
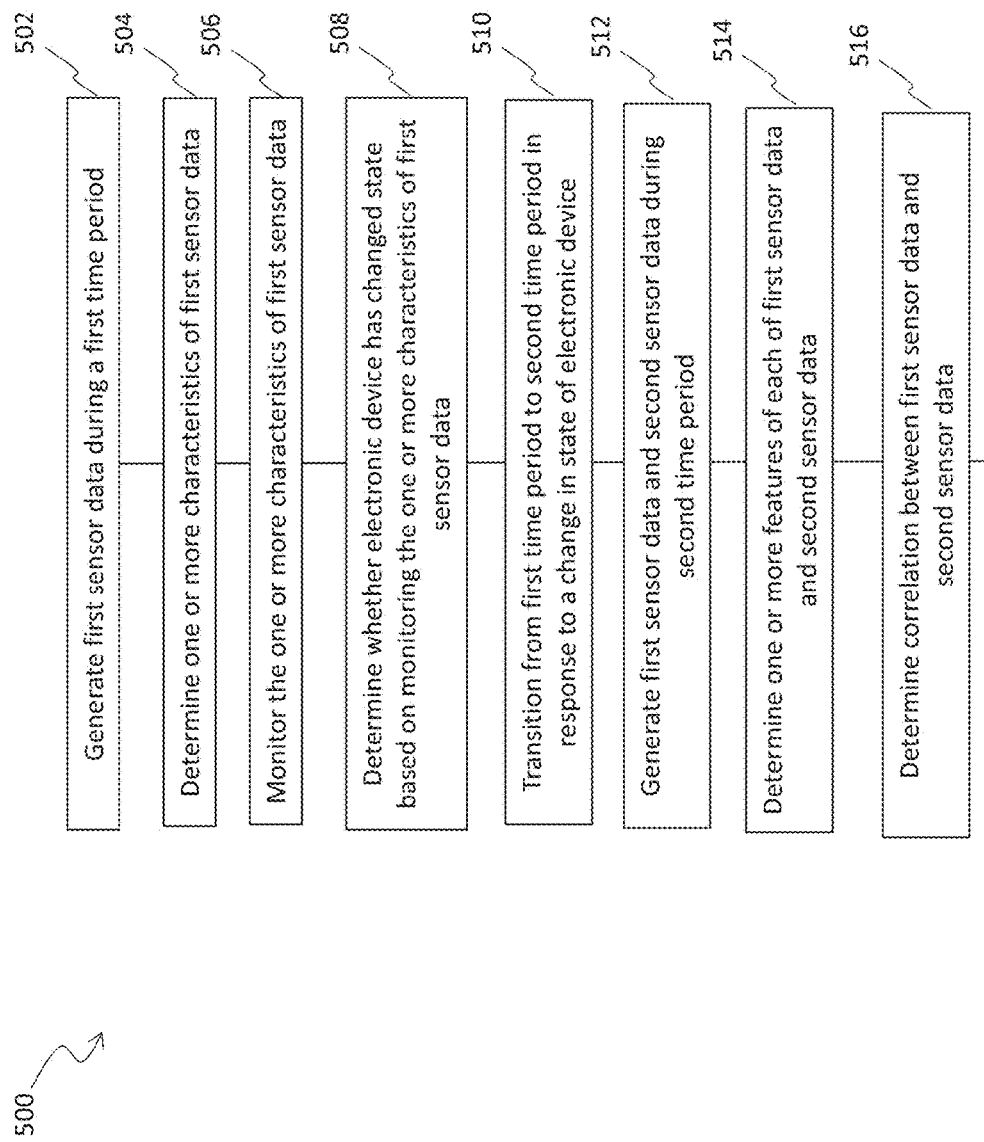
FIG. 5 shows a flow chart illustrating a method of operating the electronic device shown in FIG. 2, in accordance with an embodiment.

FIG. 2 shows a block diagram of the electronic device 102, in accordance with an embodiment. FIG. 5 shows a flow chart 500 illustrating a method of operating the electronic device 102 shown in FIG. 2, in accordance with one or more embodiments. Although the examples described in this disclosure are directed to instances where the motion of the human body is monitored, detected, and characterized, it is noted that the systems and methods described in this disclosure can also be used for monitoring, detecting, and characterizing motion of any other moving object, animate or inanimate.

The electronic device 102 may include a monitoring, detection, and characterization system 200 (hereinafter referred to as "system" for the sake of brevity). The system 200 may be configured to monitor, detect, and characterize the motion of the human body 104 based on the motion of the electronic device 102. For example, since the electronic device 102 is secured to a part of the human body 104 as shown in the embodiment of FIG. 1, it may be inferred that the motion of the electronic device 102 may be attributed to the motion of the human body 104.

As shown in the example of FIG. 2, the system 200 includes a first sensor 202, a second sensor 204, a processor 206, a controller 208, and a classifying circuit 210. In some embodiments, the system 200 may additionally include memory 212 communicatively coupled to at least one of the processor 206 or the classifying circuit 210. As a brief initial overview, the system 200 shown in FIG. 2 may be operated using the method shown in FIG. 5.

As shown in FIG. 5 in step 502 and in connection to FIG. 2, the first sensor 202 generates first sensor data 202x, 202y, 202z during a first time period (e.g. a monitoring period). During this first time period, the first sensor 202 is turned on or enabled, while the second sensor 204 is turned off or disabled. The processor 206 may subsequently determine one or more characteristics of the first sensor data 202x, 202y, 202z (e.g. as shown in FIG. 5 in step 504). In some embodiments, the one or more characteristics determined by the processor 206 may be indicative of a state of the electronic device 102 during the first time period. For example, the electronic device 102 may be in a stationary or rest state, and the one or more characteristics determined from the first sensor data 202x, 202y, 202z may indicate that the electronic device 102 is in a stationary or rest state during the first time period.

The one or more characteristics of the first sensor data 202x, 202y, 202z, determined by the processor 206, may be provided to the classifying circuit 210. The classifying circuit 210 may monitor the one or more characteristics (e.g. as shown in FIG. 5 in step 506) and determine whether there is a change in the one or more characteristics of the first sensor data 202x, 202y, 202z. A change in the one or more characteristics of the first sensor data 202x, 202y, 202z may indicate a change in the state of the electronic device 102 (e.g. as shown in FIG. 5 in step 508) and may signal a transition from the first time period to a second time period (e.g. a detection period) (e.g. as shown in FIG. 5 in step 510).

When a change in the one or more characteristics of the first sensor data 202x, 202y, 202z is detected by the classifying circuit 210, the classifying circuit 210 may generate a flag signal 207 that is provided to the controller 208, which may be configured to turn on or enable the second sensor 204. As such, during the second time period, both the first sensor 202 and the second sensor 204 may be turned on or enabled, with both the first sensor 202 and the second sensor 204 generating data (e.g. as shown in FIG. 5 in step 512). Second sensor data 204x, 204y, 204z and first sensor data 202x, 202y, 202z are provided to the processor 206 during the second time period. Second sensor data 204x, 204y, 204z may be different from and complementary to the first sensor data 202x, 202y, 202z, as described in further detail below.

During the second time period, the processor 206 determines one or more features of the second sensor data 204x, 204y, 204z and one or more features of the first sensor data 202x, 202y, 202z (e.g. as shown in FIG. 5 in step 514). The processor 206 additionally determines a correlation between the first sensor data 202x, 202y, 202z and the second sensor data 204x, 204y, 204z (e.g. as shown in FIG. 5 in step 516). The one or more features of the first sensor data 202x, 202y, 202z, the one or more features of the second sensor data 204x, 204y, 204z, and the correlation between the first sensor data 202x, 202y, 202z and the second sensor data 204x, 204y, 204z are provided to the classifying circuit 210. The classifying circuit 210 may subsequently determine whether a fitness activity is being performed based on the correlation between the first sensor data 202x, 202y, 202z and the second sensor data 204x, 204y, 204z (e.g. as shown in FIG. 5 in step 518). In the event that the classifying circuit 210 determines that a fitness activity is being performed, the classifying circuit 210 may further characterize or classify the motion of the human body based on at least one of the one or more features of the first sensor data 202x, 202y, 202z or the one or more features of the second sensor data 204x, 204y, 204z (e.g. as shown in FIG. 5 in step 520).

Overall power consumption is lowered since the second sensor 204 is turned on intermittently or sporadically. Additionally, accuracy of motion detection and characterization is increased since the classifying circuit 210 uses data from the first sensor 202, complementary data from the second sensor 204, and the correlation between such data to characterize the motion of the human body. Even further, since data from both the first sensor 202 and the second sensor 204 are used by the processor 206 and the classifying circuit 210, the system 200 may be used in a wide range of applications where motion of an object may need to be characterized or classified. This brief initial overview of the operation of the system 200 is discussed in greater detail in the description that follows.

Referring back to FIG. 2, the first sensor 202 may be a motion sensor, such as an accelerometer or a device configured to sense vibration or acceleration of the electronic device 101, for example. The first sensor 202 may generate first sensor data 202x, 202y, 202z, which may be time series data that is indicative of vibration or acceleration of the electronic device 102 in at least one of the lateral axis (e.g. referred to as the "x axis"), longitudinal axis (e.g. referred to as the "y axis"), or vertical or normal axis (e.g. referred to as the "z axis"). As such, the first sensor data 202x, 202y, 202z may be a vector quantity including a plurality of (e.g. three) scalar quantities, where each scalar quantity indicates vibration or acceleration of the electronic device 102 in a respective axis of motion.

The first sensor 202 may be referred to as an always-on sensor or a primary sensor, namely a sensor that is configured to continuously generate the first sensor data 202x, 202y, 202z while the electronic device 102 is in use. For example, as discussed above in the brief initial overview, the first sensor 202 is turned on or enabled for both the first time period (e.g. the monitoring period) and the second time period (e.g. the detection period). In contrast, the second sensor 204 may be referred to as an opportunistic sensor or a secondary sensor, namely a sensor that is turned on intermittently, periodically, or sporadically while the electronic device 102 is in use. For example, as discussed above in the brief initial overview, the second sensor 204 is turned on or enabled for the second time period (e.g. the detection period), but is turned off or disabled for the first time period (e.g. the monitoring period).

The first sensor 202 and the second sensor 204 may differ in their respective power consumption. For example, the power consumption of the first sensor 202 (e.g. over a period of time) may be less than the power consumption of the second sensor 204 (e.g. over the same period of time). As described below in greater detail, the second sensor 204 may be a sensor of a different type than the first sensor 202, thereby ensuring that second sensor data 204x, 204y, 204z is of a different type compared to first sensor data 202x, 202y, 202z.

The first sensor data 202x, 202y, 202z may be time series data having a plurality of samples. In other words, the first sensor data 202x, 202y, 202z may be generated by sampling an analog signal generated by the first sensor 202. In such embodiments, the first sensor 202 may include a sampling circuit therein. The sampling circuit may be implemented using one or more sampling circuits known in the art (e.g. a sample-and-hold circuit). In an embodiment, the sampling frequency may depend, at least in part, on an average frequency of fitness activities (e.g. about 5 Hz). As such, to fulfill the Nyquist sampling theorem, the rate at which the analog signal of the first sensor 202 is sampled may be greater than or equal to about 10 Hz (e.g. about 25 Hz in an embodiment).

In some embodiments, the first sensor data 202x, 202y, 202z may be filtered and processed prior to providing the first sensor data 202x, 202y, 202z to the processor 206. Such filtering and processing may be needed to reject low frequency drift that may be present in the analog signal generated by the first sensor 202. For example, a first low pass filter may be used to isolate the low frequency drift. The output of the first low pass filter may be subtracted from the first sensor data 202x, 202y, 202z to yield a compensated first sensor data 202x, 202y, 202z. The first low pass filter may be included in the first sensor 202 or may be external to the first sensor 202. In the example where the first low pass filter is external to the first sensor 202, the first low pass filter may be coupled between the first sensor 202 and the processor 206. The cutoff frequency of the first low pass filter may depend, at least in part, on the average frequency of fitness activities. As an illustration, the average frequency of a fitness activity (e.g. a bicep curl) may be about 5 Hz or more, and the cutoff frequency of the first low pass filter may be about 3 Hz. In some implementations, the first low pass filter may be an infinite impulse response (IIR) filter (e.g. a Butterworth filter). Since real-time monitoring, detection, and characterization of the motion of the human body may be desired, a forward-backward filtering may be applied to avoid introducing a time-delay that may be attributed to the filtering.

The first sensor data 202x, 202y, 202z (e.g. the compensated first sensor data) is provided to the processor 206, which may determine one or more characteristics (e.g. statistical characteristics) of the first sensor data 202x, 202y, 202z (e.g. as in step 504 shown in FIG. 5). As an example, the processor 206 may determine at least one of the energy, periodicity, frequency shift, or a change in angle of the first sensor data 202x, 202y, 202z. As described above in the brief initial overview, the one or more characteristics determined by the processor 206 may be indicative of a state of the electronic device 102.

Figure 3:
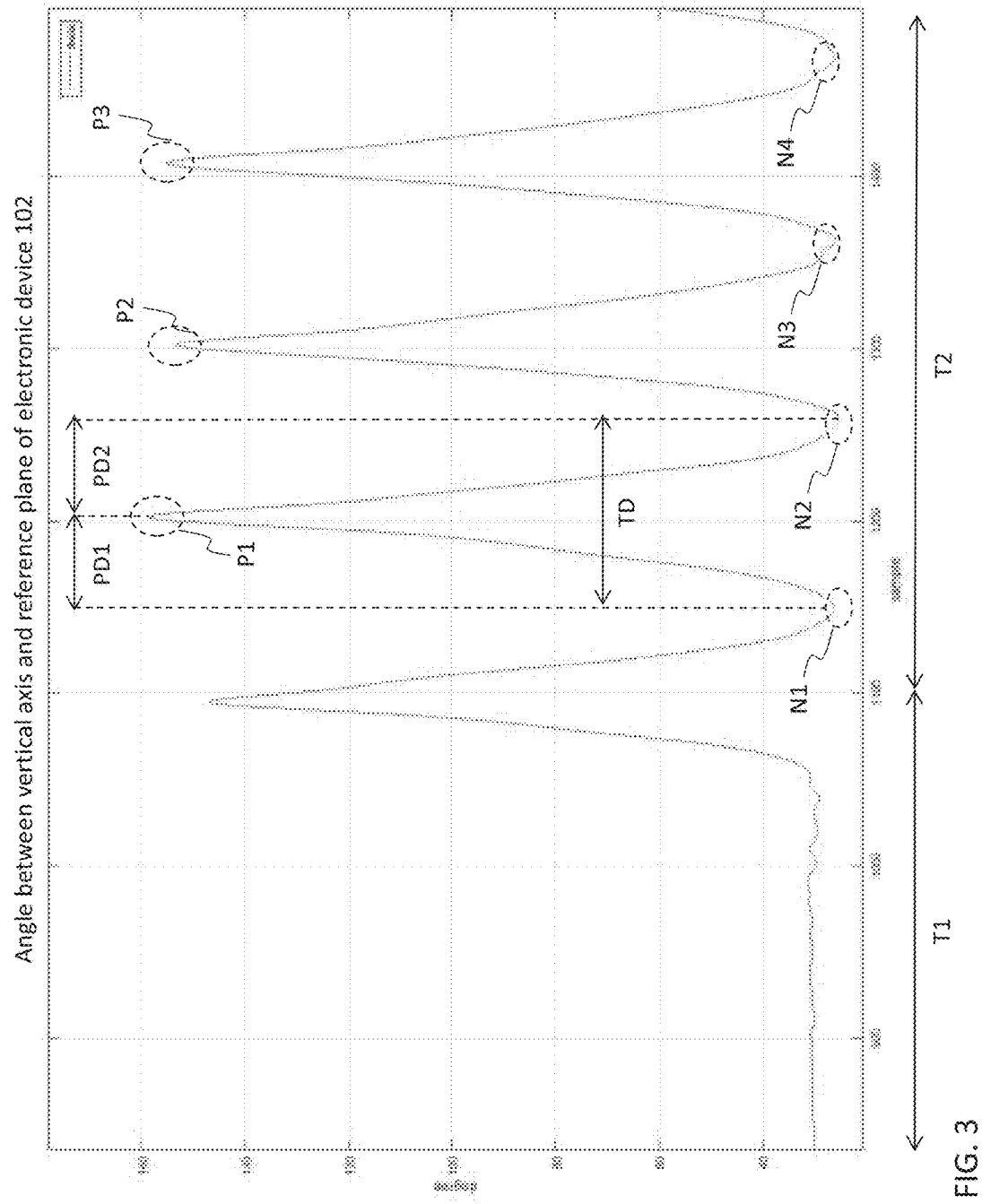
FIG. 3 illustrates the variation, with respect to time, of an angle between a vertical axis and a reference plane of the electronic device shown in FIG. 1, in accordance with an embodiment.

FIG. 3 illustrates an example where the one or more characteristics of the first sensor data 202x, 202y, 202z, determined by the processor 206, includes an angle θ between a vertical axis and a reference plane of the electronic device 102, in accordance with an embodiment. The plot in FIG. 3 uses a Cartesian-coordinate system, where the y-axis is a linear scale denoting the angle θ (expressed in degrees) and the x-axis is a linear scale denoting time (expressed as sample number). The angle θ determined by the processor 206 during the first time period T1 (e.g. the monitoring period) is depicted in FIG. 3 for samples 800 to 1100. It is noted that the first time period T1 also includes samples 1 to 799, and the variation of the angle θ for samples 1 to 799 is similar to the variation seen in FIG. 3 for samples 800 to 1100. Samples 1 to 799 are omitted from FIG. 3 so as to highlight salient features of the first time period T1 and a second time period T2.

In the example shown in FIG. 3, the processor 206 receives the first sensor data 202x, 202y, 202z from the first sensor 202 and determines the angle θ based on the first sensor data 202x, 202y, 202z. Suppose each sample of the first sensor data 202x, 202y, 202z is denoted by the index n, each sample of the lateral axis of first sensor data 202x is denoted by AccX[n], each sample of the longitudinal axis of first sensor data 202y is denoted by AccY[n], and each sample of the normal axis of first sensor data 202z is denoted by AccZ[n]. Then, the angle θ between the vertical axis and the reference plane of the electronic device 102 may be determined, by the processor 206, for each sample n by performing the following mathematical operation: $\theta(n) = \cos^{-1}(\alpha(n) \cdot Pd)$, where $\alpha(n) = [AccX[n] \, AccY[n] \, AccZ[n]]/|Acc[n]|, Pd = [0\text{-}10]^T$, $|Acc[n]| = \sqrt{(AccX[n])^2 + (AccY[n])^2 + (AccZ[n])^2}$, and $(a(n) \cdot Pd)$ denotes the dot product between vectors a(n) and Pd. In some embodiments, the vector Pd may be stored in the memory 212 and provided to the processor 206 in response to a request by the processor 206 to the memory 212.

In some embodiments, a mean value μ and a standard deviation σ of each of the one or more characteristics (e.g. the angle θ) of the first sensor data 202x, 202y, 202z may be stored in the memory 212. The mean value μ and the standard deviation σ may be preloaded (e.g. based on default values observed for a population of fitness enthusiasts). In some embodiments, the classifying circuit 210 may update (e.g. continuously update) the mean value μ and the standard deviation σ based on the individual characteristics, usage, or behavior of the user of the electronic device 102 over a period of time. In some examples, the processor 206 may additionally determine a probability that a change in the state of the electronic device 102 has occurred. In this connection, the processor 206 may determine a p-value or a z-value, for each sample n, based on the value of the respective characteristic (e.g. the angle θ) at a particular sample n, the mean value μ, and the standard deviation σ.

As described above in the brief initial overview, the processor 206 may provide the one or more characteristics (e.g. the angle θ) determined from the first sensor data 202x, 202y, 202z to the classifying circuit 210. In examples where the processor 206 additionally determines the probability that a change in the state of the electronic device 102 has occurred, the processor 206 may also provide the determined probabilities (e.g. p-value or z-value) to the classifying circuit 210. The classifying circuit 210 monitors the one or more characteristics (e.g. the angle θ) and, possibly, the probabilities determined by the processor 206 to determine whether a change in the state of the electronic device 102 has occurred (e.g. as in steps 506 and 508 of FIG. 5). As observed in FIG. 3, the three-dimensional vector quantity of the first sensor data 202x, 202y, 202z is reduced to a one-dimensional quantity (e.g. the angle θ), thereby allowing for low computation cost and small footprint in monitoring the one or more characteristics of the first sensor data 202x, 202y, 202z.

The classifying circuit 210 may be a machine learning classifier implemented using machine learning techniques, examples being a decision tree, linear regression, logistic regression, support vector machine (SVM), naive Bayes, k-nearest neighbors, k-means, random forest, gradient boost, among others. To further enhance the accuracy of the determination of whether the electronic device 102 has changed state, the classifying circuit 210 may implement a time-based voting method. Referring to the example in FIG. 3, it is observed that the variation in the angle θ is minimal from samples 800 to 1050. As such, the classifying circuit 210 may monitor the angle θ computed by the processor 207 and determine that no change in the state of the electronic device 102 has occurred up to sample 1050. However, in the plot shown in FIG. 3, the angle θ changes drastically between samples 1050 and 1100. This change in the angle θ may result in a large deviation of the angle θ from its mean value μ at a rest state. In some embodiments, a deviation of more than two standard deviations may indicate that a change in the state of the electronic device 102 has occurred. Stated differently, the probabilities (e.g. p-value or z-value) determined by the processor 206 may be vary drastically between samples 800 to 1050 and samples 1050 and 1100, thereby indicating that the electronic device 102 has changed its state (e.g. from a rest state to an active state).

As described above in the brief initial overview, a change in the state of the electronic device 102 may signal a transition from the first time period T1 to a second time period T2 (e.g. the detection period) (e.g. as in step 510 of FIG. 5). Additionally, the classifying circuit 210 may generate the flag signal 207 that is provided to the controller 208. The controller 208 may be configured to turn on or enable the second sensor 204 in response to receiving the flag signal 207, thereby allowing for data to be generated by the second sensor 204 (e.g. as in step 512 of FIG. 5).

The second sensor 204 may be a sensor of a different type than the first sensor 202. For example, the first sensor 202 may be an accelerometer, while the second sensor 204 may be a sensor other than an accelerometer (for example, at least one of a magnetometer, pressure sensor, gyroscope, humidity sensor, or microphone). When the second sensor 204 is turned on or enabled, the second sensor 204 may generate second sensor data 204x, 204y, 204z, which may be time series data that is indicative of an altitude (e.g. in the example of a pressure sensor) or orientation (e.g. in the example of a gyroscope) of the electronic device 102 in at least one of the lateral axis (e.g. referred to as the "x axis"), longitudinal axis (e.g. referred to as the "y axis"), or vertical or normal axis (e.g. referred to as the "z axis"). In some examples, the second sensor data may be a scalar quantity (e.g. where the second sensor 204 is a pressure sensor). Similar to the first sensor data 202x, 202y, 202z, the second sensor data 204x, 204y, 204z may be time series data having a plurality of samples. In some examples, the analog signal sensed by the first sensor 202 and the analog signal sensed by the second sensor 204 are sampled at the same sampling rate (e.g. about 25 Hz).

Figure 4:
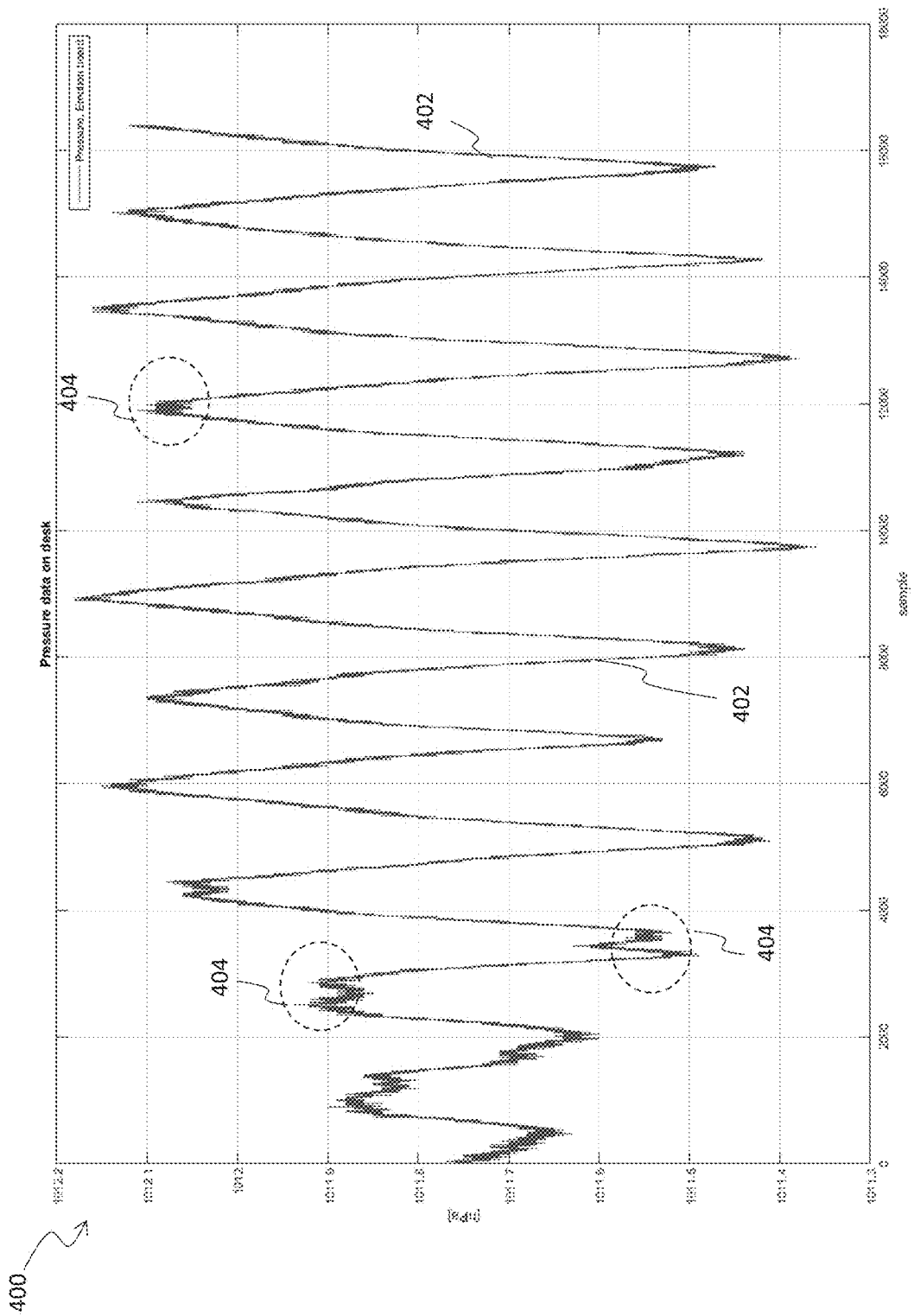
FIG. 4 shows an example of scalar data generated by the second sensor shown in FIG. 2, in accordance with an embodiment.

In some embodiments, the second sensor data 204x, 204y, 204z may be filtered prior to providing the second sensor data 204x, 204y, 204z to the processor 206. Such filtering may be needed to reject at least one of low frequency drift or high frequency noise that may be present in the analog signal generated by the second sensor 204. FIG. 4 shows an example of scalar second sensor data obtained from the second sensor 204 in an embodiment where the second sensor 204 is a pressure sensor. The plot in FIG. 4 uses a Cartesian-coordinate system, where the y-axis is a linear scale denoting pressure (expressed in hectopascal, hPa) and the x-axis is a linear scale denoting time (expressed as sample number). The pressure sensor data shown in FIG. 4 was obtained in an experiment where the second sensor 204 (e.g. pressure sensor) was kept stationary on a table. As shown in FIG. 4, a low frequency drift 402 (manifesting itself as a sinusoidal variation) and high frequency noise components 404 are observed in the second sensor data 204x, 204y, 204z even when the second sensor 204 is stationary.

In order to compensate for low frequency drift, a second low pass filter may be used.

The output of the second low pass filter may be subtracted from the second sensor data 204x, 204y, 204z to yield a drift-compensated second sensor data 204x, 204y, 204z. The second low pass filter may be included in the second sensor 204 or may be external to the second sensor 204. In the example where the second low pass filter is external to the second sensor 204, the second low pass filter may be coupled between the second sensor 204 and the processor 206.

The cutoff frequency of the second low pass filter may depend, at least in part, on an average frequency of fitness activities and the frequency content of the low frequency drift 402 present in the second sensor data 204x, 204y, 204z. As an example, referring to FIG. 4, the low frequency drift 402 has a frequency of about 0.016 Hz, and in general, the low frequency drift 402 may have frequency content less than about 0.1 Hz. As such, the frequency content of the low frequency drift 402 may need to be within the passband of the second low pass filter in order to ensure that the second low pass filter effectively removes the low frequency drift 402 of the second sensor data 204x, 204y, 204z. Furthermore, fitness activities are generally performed between about 0.5 Hz and 1.5 Hz. As such, frequencies above 0.5 Hz may need to be within the stopband of the second low pass filter to ensure that the subtraction between the output of the second low pass filter and the second sensor data 204x, 204y, 204z preserves frequencies within the 0.5 Hz and 1.5 Hz range. Based on these considerations, the second low pass filter may have a cut off frequency of about 0.4 Hz. This choice will allow separation of 0.01. Hz and 0.5. Hz, gives a band width of 0.1 Hz with respect to frequency corresponding to fitness activities, and also has coefficients that are of order $10^{-2}$ thereby causing very minimal numerical instability. In some implementations, the second low pass filter may be a Butterworth filter.

In order to compensate for high frequency noise, the drift-compensated second sensor data 204x, 204y, 204z can be low pass filtered (e.g. by a third low pass filter) to yield a drift- and high frequency noise-compensated second sensor data 204x, 204y, 204z. The third low pass filter may be included in the second sensor 204 or may be external to the second sensor 204. In the example where the third low pass filter is external to the second sensor 204, the third low pass filter may be coupled between the second low pass filter (described above) and the processor 206. The cutoff frequency of the third low pass filter may depend, at least in part, on an average frequency of fitness activities. For example, as mentioned above, fitness activities are generally performed between about 0.5 Hz and 1.5 Hz. As an illustration, for most exercises like bicep curls, pushups, sit-ups, squats, an individual typically requires at least about 1 second to complete a single repetition. In cases of an extremely fit or strong individual, a single repetition may be performed in about 0.5 seconds. As such, frequency components beyond about 2 Hz may not be useful. Based on these considerations, the third low pass filter may have a cut off frequency of about 2 Hz. In some implementations, the third low pass filter may be a Butterworth filter.

During the second time period T2, both the first sensor 202 and the second sensor 204 may be turned on or enabled. Second sensor data 204x, 204y, 204z and first sensor data 202x, 202y, 202z are provided to the processor 206 during the second time period T2 (e.g. as in step 512 of FIG. 5). During the second time period T2, the processor 206 determines one or more features of the second sensor data 204x, 204y, 204z and one or more features of the first sensor data 202x, 202y, 202z (e.g. as in step 514 of FIG. 5).

As an example of the one or more features of the first sensor data 202x, 202y, 202z that may be determined by the processor 206 during the second time period $T_2$, referring back to FIG. 3, the processor 206 may continue to determine the angle θ during the second time period T2 and may additionally apply detection logic (e.g. peak detection logic) to the angle θ to generate the one or more features of the first sensor data 202x, 202y, 202z. For example, during the second time period T2, periodic patterns in the angle θ may be identified (e.g. due to the repetitive nature of most fitness activities). As shown in FIG. 3, the angle θ may include a plurality of positive peaks P1, P2, P3 and a plurality of negative peaks N1, N2, N3, N4 during the second time period T2. The processor 206 may determine a total duration TD, which may be the number of samples between two consecutive negative peaks (e.g. the number of samples between negative peaks N1 and N2). In some embodiments, the total duration TD may be indicative of the period of the first sensor data 202x, 202y, 202z. In the illustration of FIG. 3, the total duration TD may be about 100 samples.

Additionally or alternatively, the processor 206 may determine a first duration PD1, which may be the number of samples between the first negative peak N1 and the subsequent positive peak P1. In the illustration of FIG. 3, the first phase duration PD1 may be about 50 samples. Additionally or alternatively, the processor 206 may determine a first phase slope, which may be the rate of change of the angle θ between the first negative peak N1 and the subsequent positive peak P1. Additionally or alternatively, the processor 206 may determine a second phase duration PD2, which may be the number of samples between the subsequent positive peak P1 and the next negative peak N2. In the illustration of FIG. 3, the second phase duration PD2 may be about 50 samples. Additionally or alternatively, the processor 206 may determine a second phase slope, which may be the rate of change of the angle θ between the subsequent positive peak P1 and the next negative peak N2. Additionally or alternatively, the processor 206 may determine a maximum angle change, which may be the maximum difference between a positive peak (e.g. positive peak P2) and an adjacent negative peak (e.g. negative peak N2). For example, in the illustration of FIG. 3, the maximum angle change (e.g. peak-to-peak value) may be about 130 degrees (e.g. obtained from the difference between the angle at positive peak P2, which is about 160 degrees, and the angle at negative peak N2, which is about 30 degrees). Additionally or alternatively, the processor 206 may determine a start index, which may be the sample corresponding to the negative starting peak. In the illustration of FIG. 3, the negative peak N1 corresponding to approximately sample 1150 may be the negative starting peak, and therefore, the start index may about 1150. Additionally or alternatively, the processor 206 may determine a stop index, which may be the sample corresponding to the negative ending peak. In the illustration of FIG. 3, the negative peak N4 corresponding to approximately sample 1475 may be the negative ending peak, and therefore, the stop index may about 1475. Additionally or alternatively, the processor 206 may determine a middle index, which may be the sample corresponding to any positive peak between the negative ending peak N4 and the negative starting peak N1.

Similar to the processing performed on the first sensor data 202x, 202y, 202z, the processor 206 may apply detection logic (e.g. peak detection logic, as discussed above) to the second sensor data 204x, 204y, 204z received from the second sensor 204. As an example, the processor 206 may similarly determine, from the second sensor data 204x, 204y, 204z, at least one of a first duration, first phase duration, a first phase slope, a second phase duration, a second phase slope, a maximum peak-to-peak value, a start index, a stop index, or a middle index of the second sensor data 204x, 204y, 204z (e.g. the pressure data shown in FIG. 4).

It is noted that since the second sensor 204 is of a different type than the first sensor 202, the second sensor data 204x, 204y, 204z may be different from the first sensor data 202x, 202y, 202z. Nonetheless, the second sensor data 204x, 204y, 204z may be complementary to the first sensor data 202x, 202y, 202z in that similar periodic patterns may be observed in the second sensor data 204x, 204y, 204z in the event that a fitness activity is being engaged in. As such, variations that occur in the first sensor data 202x, 202y, 202z may also be observed in second sensor data 204x, 204y, 204z, which is a measurement independent from the first sensor data 202x, 202y, 202z. In this connection, the processor 206 may further determine a correlation between the first sensor data 202x, 202y, 202z and the second sensor data 204x, 204y, 204z (e.g. as in step 516 of FIG. 5). In order to avoid false positives, the correlation between the first sensor data 202x, 202y, 202z and the second sensor data 204x, 204y, 204z may be determined on every positive peak of at least one of the first sensor data 202x, 202y, 202z or the second sensor data 204x, 204y, 204z.

The correlation between the first sensor data 202x, 202y, 202z and the second sensor data 204x, 204y, 204z may be expressed as a correlation coefficient. The correlation coefficient, the one or more features of the first sensor data 202x, 202y, 202z, and the one or more features of the second sensor data 204x, 204y, 204z may be provided to the classifying circuit 210. The classifying circuit 210 subsequently determines whether a fitness activity is being engaged in (e.g. as in step 518 of FIG. 5) and, if so, the classifying circuit 210 further characterizes (or classifies) the motion of the human body (e.g. as in step 520 of FIG. 5). For example, as discussed above, the classifying circuit 210 may be a machine learning classifier implemented using machine learning techniques. The classifying circuit 210 may initially determine whether the correlation between the first sensor data 202x, 202y, 202z and the second sensor data 204x, 204y, 204z is strong enough to determine that a fitness activity is being engaged in. In some embodiments, this may require a comparison of the correlation coefficient obtained from the correlation between the first sensor data 202x, 202y, 202z and the second sensor data 204x, 204y, 204z with a coefficient threshold (e.g. 0.5). In some embodiments, the classifying circuit 210 may update the coefficient threshold based on the individual characteristics, usage, or behavior of the user of the electronic device 102 over a period of time. In the event that the correlation coefficient is equal to or greater than the coefficient threshold, the classifying circuit 210 may determine that a fitness activity is being performed. In such a scenario, the classifying circuit 210 may further characterize or classify, based on machine learning techniques (e.g. based on motion signatures that may be pre-loaded in the memory 212), the motion of the human body based on the one or more features of the first sensor data 202x, 202y, 202z and the one or more features of the second sensor data 204x, 204y, 204z (e.g. a first phase duration, a first phase slope, a second phase duration, a second phase slope, a maximum peak-to-peak value, a start index, a stop index, or a middle index). As an example, the classifying circuit 210 may characterize the motion of the human body as being a bicep curl, a push up, a squat, a driving activity, or a biking activity based on the one or more features of the first sensor data 202x, 202y, 202z and the one or more features of the second sensor data 204x, 204y, 204z.

In some embodiments, the system 200 may additionally include a counter 214, which may be updated or incremented based on the characterization or classification determined by the classifying circuit 210. As an example, in the case where the classifying circuit 210 determines that a bicep curl, a push up, or a squat is being performed, the counter 214 may be incremented, based on the one or more features of the first sensor data 202x, 202y, 202z and the one or more features of the second sensor data 204x, 204y, 204z, to indicate, to the user, the number of repetitions of the fitness activity performed.

In some embodiments, the classifying circuit 210 may further generate a metric that is indicative of the accuracy of confidence of the characterization or classification determined by the classifying circuit 210. As an example, the classifying circuit 210 may determine a confidence interval that indicates the degree of certainty associated with its characterization or classification. In response to the metric being greater than a threshold (e.g. indicating high confidence in its characterization or classification), the classifying circuit 210 may modify the flag signal 207 provided to the controller 208. The modified flag signal 207 may trigger the controller 208 to turn off the second sensor 204, thereby disabling the high power sensor of the system 200 and conserving power. In such a scenario, the first sensor 202 continues to be turned on and enabled, and the processor 206 continues to process the first sensor data 202x, 202y, 202z in order to continue determining the one or more features of the first sensor data 202x, 202y, 202z (e.g. a first phase duration, a first phase slope, a second phase duration, a second phase slope, a maximum peak-to-peak value, a start index, a stop index, or a middle index) so as to increment the counter 214 and/or monitor the fitness activity.

Based on the description given above, the system 200 and the method of operating the system 200 allows for high power sensors (e.g. the second sensor 204) to be turned on whenever there is an opportunity to obtain complementary data to enable characterization and classification to be performed with high accuracy. Overall power consumption is lowered since the second sensor 204 is turned on intermittently or sporadically. Additionally, accuracy of motion detection and characterization is increased since the classifying circuit 210 uses data from the first sensor 202, complementary data from the second sensor 204, and the correlation between such data to characterize the motion of the human body. Even further, since data from both the first sensor 202 and the second sensor 204 are used by the processor 206 and the classifying circuit 210, the system 200 may be used in a wide range of applications where motion of an object may need to be characterized or classified.

Figure 6:
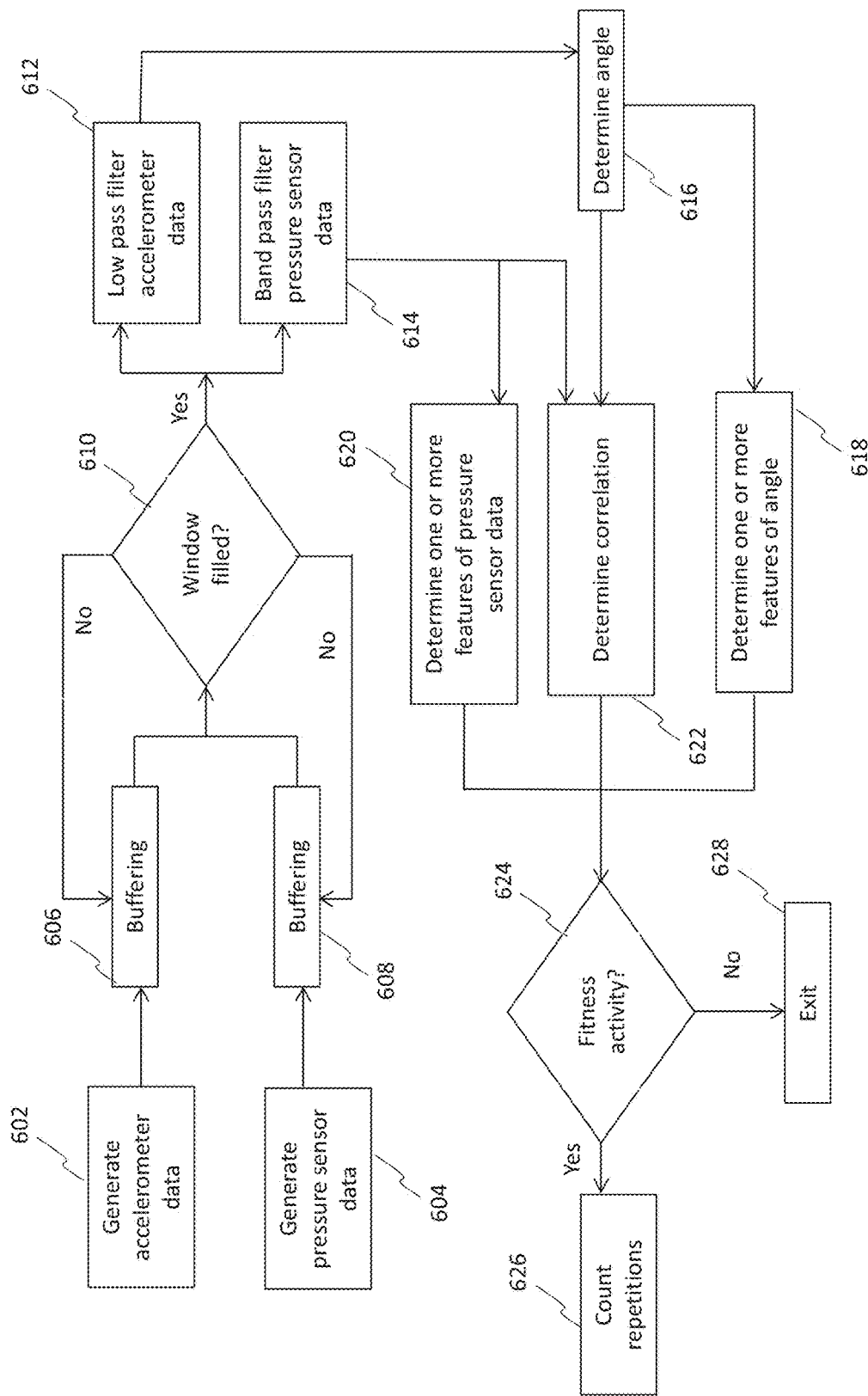
FIG. 6 shows a flow chart illustrating a method of operating the electronic device shown in FIG. 2 during a feature-detection period, in accordance with an embodiment.

FIG. 6 shows a flow chart 600 illustrating a method of operating the system 200 shown in FIG. 2 during the second time period T2 (e.g. detection period), in accordance with an embodiment. The example shown in FIG. 6 illustrates an embodiment where the first sensor 202 is an accelerometer, the second sensor 204 is a pressure sensor, and where real-time processing is performed by the processor 206. As shown in FIG. 6, the method includes generating accelerometer data (in step 602) and generating pressure sensor data (in step 604). In order for the processor 206 to process the first sensor data 202x, 202y, 202z and the second sensor data 204x, 204y, 204z in real-time, it may be possible to buffer each of the first sensor data 202x, 202y, 202z and the second sensor data 204x, 204y, 204z into fixed length buffers (e.g. in steps 606 and 608). For example, each time a new sample is acquired from the pressure sensor and the accelerometer, the respective sample contributes to fill the respective buffer. In some embodiments, each buffer may include samples from a 5 to 6 seconds time window. Furthermore, in order to avoid possible loss of accelerometer data, consecutive buffer windows in step 606 may overlap (e.g. up to about 50%). Similarly, in order to avoid possible loss of pressure sensor data, consecutive buffer windows in step 608 may overlap (e.g. up to about 50%).

When the buffer windows are filled (e.g. in step 610), the accelerometer data may be low pass filtered (e.g. in step 612) to compensate for low frequency drift, as discussed above in respect of FIGS. 2 to 5. Additionally, the pressure sensor data may be band pass filtered (e.g. in step 614) to compensate for low frequency drift and high frequency noise components, as discussed above in respect of FIGS. 2 to 5. The processor 206 may determine the angle θ, discussed above in respect of FIG. 3, based on the filtered accelerometer data (e.g. in step 616). Subsequently, one or more features of the angle may be determined (e.g. in step 618), as discussed above in respect of FIG. 3. Additionally, one or more features of the pressure sensor data may be determined (e.g. in step 620), as discussed above in respect of FIG. 4. A correlation between the accelerometer data and the pressure sensor data may be determined as well (e.g. in step 622), as discussed above in respect of FIGS. 2 to 5. The one or more features of the pressure sensor data, the one or more features of the angle and the correlation coefficient may be provided to the classifying circuit 210, which determines whether a fitness activity is being performed (e.g. in step 624). In the event of a positive determination, the number of repetitions is counted (e.g. in step 626). On the other hand, in the event of a negative determination, the method is exited (e.g. in step 628), and the pressure sensor may be turned off (e.g. to save power).

As an example of the detection of a bicep curl, the first sensor 202 (e.g. the always on, low power sensor) may be an accelerometer, while the second sensor 204 (e.g. the opportunistic, high power sensor) may be a pressure sensor. The classifying circuit 210 may monitor the angle from a vertical axis, determined from the accelerometer data, to detect a change in the angle. In the event that such a change is detected, the pressure sensor is turned on in order to get information on a change in height or altitude, thereby providing complementary data to the angle data obtained from the accelerometer. In the event that the correlation between the pressure sensor data and the accelerometer data is high (e.g. greater than 0.5), the classifying data may determine that a bicep curl is being performed.

As an example of the detection of a pushup, the first sensor 202 (e.g. the always on, low power sensor) may be an accelerometer, while the second sensor 204 (e.g. the opportunistic, high power sensor) may be a gyroscope. The classifying circuit 210 may monitor the periodicity in the acceleration and changes in amplitude, determined from the accelerometer data, to detect a change in the state of the electronic device. In the event that such a change is detected, the gyroscope is turned on in order to get information on a change in angle, thereby providing complementary data to the acceleration data obtained from the accelerometer. In the event that the change in angle from one period to the next matches pre-stored values (e.g. in the memory 212), the classifying data may determine that a pushup is being performed.

As an example of the detection of a squat, the first sensor 202 (e.g. the always on, low power sensor) may be an accelerometer, while the second sensor 204 (e.g. the opportunistic, high power sensor) may be a pressure sensor. The classifying circuit 210 may monitor the periodicity in the vertical acceleration, determined from the accelerometer data, to detect a change in the state of the electronic device. In the event that such a change is detected, the pressure sensor is turned on in order to get information on a change in height, thereby providing complementary data to the acceleration data obtained from the accelerometer. In the event that the change in height (obtained from the pressure sensor) is substantially equal to the estimated change in height (obtained from processing vertical acceleration data), the classifying data may determine that a squat is being performed.

As discussed above, the system 200 may be extended beyond the detection and characterization of fitness activity. For example, the system 200 may be used to determine whether a user is driving or biking. As an example, the first sensor 202 (e.g. the always on, low power sensor) may be an accelerometer, while the second sensor 204 (e.g. the opportunistic, high power sensor) may be a gyroscope. The classifying circuit 210 may monitor statistical features (such as mean, variance, vertical acceleration, maximum and minimum changes thereof), determined from the accelerometer data, to detect a change in the state of the electronic device. In the event that such a change is detected, the gyroscope is turned on in order to get information on a rate of change in acceleration. In the event that the rate of change in acceleration is greater than a threshold (e.g. stored in the memory 212), the classifying data may determine that biking is being performed.

In an embodiment, a device may include a first sensor configured to generate first sensor data during a first time period and a second time period; a second sensor configured to be disabled during the first time period, the second sensor further being configured to generate second sensor data during the second time period; and a processor configured to determine a characteristic of the first sensor data during the first time period. The device may further include a classifying circuit configured to determine, during the first time period, whether the device has changed state based on the characteristic of the first sensor data, the classifying circuit further being configured to cause the second sensor to be enabled in response to a change in a state of the device.

In an embodiment, a method may include generating first sensor data during a first time period; determining whether an electronic device has changed state based on the first sensor data, wherein a transition from the first time period to a second time period occurs in response to a determination that the electronic device has changed state; and generating the first sensor data and second sensor data during the second time period. The method may further include determining one or more features of each of the first sensor data and the second sensor data; and characterizing a motion of a human body based on at least one of the one or more features of the first sensor data or the one or more features of the second sensor data.

In an embodiment, a device may include an accelerometer configured to generate accelerometer data during a first state of the device and a second state of the device; a sensor, different from the accelerometer, configured to generate sensor data during the second state of the device; and a processor configured to determine one or more features of the accelerometer data and one or more features of the sensor data during the second state of the device. The device may further include a classifying circuit configured to characterize a motion of a human body based on at least one of the one or more features of the accelerometer data and the one or more features of the sensor data.

Those of skill in the art will further appreciate that the various illustrative logical blocks, modules, circuits, and algorithms described in connection with the embodiments disclosed herein may be implemented as electronic hardware, instructions stored in memory or in another computer-readable medium and executed by a processor or other processing device, or combinations of both. The devices and processing systems described herein may be employed in any circuit, hardware component, integrated circuit (IC), or IC chip, as examples. Memory disclosed herein may be any type and size of memory and may be configured to store any type of information desired. To clearly illustrate this interchangeability, various illustrative components, blocks, modules, circuits, and steps have been described above generally in terms of their functionality. How such functionality is implemented depends upon the particular application, design choices, and/or design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a processor, a digital signal processor (DSP), an Application Specific Integrated Circuit (ASIC), a field programmable gate array (FPGA) or other programmable logic device, discrete gate or transistor logic, discrete hardware components, or any combination thereof designed to perform the functions described herein. A processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The embodiments disclosed herein may be embodied in hardware and in instructions that are stored in hardware, and may reside, for example, in Random Access Memory (RAM), flash memory, Read Only Memory (ROM), Electrically Programmable ROM (EPROM), Electrically Erasable Programmable ROM (EEPROM), registers, a hard disk, a removable disk, a CD-ROM, or any other form of computer-readable medium known in the art. An exemplary storage medium is coupled to the processor such that the processor can read information from, and write information to, the storage medium. In the alternative, the storage medium may be integral to the processor. The processor and the storage medium may reside in an ASIC.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A device, comprising:
    a first sensor configured to generate first sensor data during a first time period and a second time period;
    a second sensor configured to be disabled during the first time period, the second sensor further being configured to generate second sensor data during the second time period;
    a processor coupled to an output of the first sensor and an output of the second sensor, the processor being configured to determine a characteristic of the first sensor data during the first time period; and
    a classifying circuit coupled to an output of the processor, the classifying circuit being configured to determine whether the device has changed state based on the characteristic of the first sensor data during the first time period after determining the characteristic of the first sensor data, wherein the change in the state of the device excludes characterization of motion of a human body,
    in response to determining that the state of the device has changed, sending a signal to the processor to enable the second sensor during the second time period, and
    after enabling the second sensor, identify a type of motion of the human body using both the first sensor data and the second sensor data during the second time period.

2. The device of claim 1, wherein the first sensor comprises an accelerometer.

3. The device of claim 1, wherein the second sensor comprises at least one of a pressure sensor, a gyroscope, a humidity sensor, or a microphone.

4. The device of claim 1, wherein a power consumption of the first sensor during a predetermined time period is less than a power consumption of the second sensor during the predetermined time period.

5. The device of claim 1, wherein the characteristic of the first sensor data comprises at least one of an energy, a periodicity, a frequency shift, or a change in angle of the first sensor data.

6. The device of claim 1, wherein the processor is further configured to determine one or more features of the first sensor data during the second time period, one or more features of the second sensor data during the second time period, and a correlation between the first sensor data and the second sensor data during the second time period.

7. The device of claim 6, wherein the one or more features of the first sensor data comprises at least one of a period of the first sensor data, a positive rate of change of the first sensor data, a negative rate of change of the first sensor data, or a peak-to-peak value of the first sensor data.

8. The device of claim 6, wherein the one or more features of the second sensor data comprises at least one of a period of the second sensor data, a positive rate of change of the second sensor data, a negative rate of change of the second sensor data, or a peak-to-peak value of the second sensor data.

9. The device of claim 6, wherein the classifying circuit is further configured to characterize the type of motion of the human body based on the correlation between the first sensor data and the second sensor data.

10. The device of claim 9, wherein the classifying circuit is configured to characterize the motion of the human body using machine learning of one or more motion signatures of the human body.

11. A method of characterizing motion of a human body, comprising:
    generating, by a first sensor of an electronic device, first sensor data during a first time period;
    determining, by a processor of the electronic device coupled to an output of the first sensor and based on a statistic of the first sensor data, whether the electronic device has changed state based on the first sensor data, wherein the statistic of the first sensor data excludes characterization of the motion of the human body, and wherein a transition from the first time period to a second time period occurs in response to a determination that the electronic device has changed state;
    in response to determining that the electronic device has changed state based on the first sensor data, generating, by the first sensor and a second sensor of the electronic device, respectively, the first sensor data and second sensor data during the second time period;
    determining, by the processor, one or more features of each of the first sensor data and the second sensor data, wherein the processor is further coupled to an output of the second sensor, and wherein the one or more features of the first sensor data and the one or more features of the second sensor data exclude characterization of the motion of the human body; and
    subsequent to determining one or more features of each of the first sensor data and the second sensor data, characterizing, by a classifying circuit coupled to an output of the processor, a type of the motion of the human body based on both features of the first sensor data and the features of the second sensor data during the second time period.

12. The method of claim 11, further comprising:
    determining, by the processor, a correlation between the first sensor data and the second sensor data.

13. The method of claim 12, further comprising:
    determining, by the classifying circuit, whether a fitness activity is being performed based on the correlation between the first sensor data and the second sensor data.

14. The method of claim 12, the second sensor being a different type from the first sensor.

15. The method of claim 11, wherein the first sensor comprises an accelerometer, and wherein the second sensor comprises at least one of a pressure sensor, a gyroscope, a humidity sensor, or a microphone.

16. The method of claim 11, wherein an average power consumption of the first sensor is less than an average power consumption of the second sensor.

17. A device, comprising:
- an accelerometer configured to generate accelerometer data during a first state of the device and a second state of the device;
- a sensor, different from the accelerometer, configured to generate sensor data during the second state of the device;
- a processor coupled to an output of the accelerometer and an output of the sensor, the processor being configured to determine one or more features of the accelerometer data and one or more features of the sensor data during the second state of the device, wherein the one or more features of the accelerometer data and the one or more features of the sensor data exclude characterization of a motion of a human body;
- a first filter coupled between the accelerometer and the processor, the first filter configured to low pass filter the accelerometer data and provide the filtered accelerometer data to the processor;
- a second filter coupled between the sensor and the processor, the second filter configured to band pass filter the sensor data and provide the filtered sensor data to the processor; and
- a classifying circuit coupled to an output of the processor, the classifying circuit being configured to
  - determine whether the device has changed state based on the characteristic of the accelerometer data during a first state, wherein the change in the state of the device excludes the characterization of the motion of the human body,
  - in response to determining that the state of the device has changed, sending a signal to the processor to enable a second sensor during a second time period, and
  - after enabling the second sensor, identify a type of motion of a human body using both the features of the accelerometer data and the features of the sensor data during the second time period.

18. The device of claim 17, wherein the processor is further configured to determine one or more characteristics of the accelerometer data during the first state of the device, and wherein the classifying circuit is configured to determine whether the device has transitioned from the first state to the second state based on the one or more characteristics of the accelerometer data.

19. The device of claim 17, wherein the sensor comprises at least one of a pressure sensor, a gyroscope, a humidity sensor, or a microphone.

20. The device of claim 17, wherein the sensor is disabled during the first state of the device.

* * * * *